United States Patent [19]
Mermillod

[11] Patent Number: 4,918,753
[45] Date of Patent: Apr. 24, 1990

[54] ADJUSTABLE FASTENING FOR SECURING GOGGLES TO A HELMET

[75] Inventor: Jean-Francois Mermillod, Saint-Jean-De-Sixt, France

[73] Assignee: Saer-Jmp, Bischheim, France

[21] Appl. No.: 270,004

[22] Filed: Nov. 14, 1988

[30] Foreign Application Priority Data

Nov. 13, 1987 [FR] France .................. 87 15724

[51] Int. Cl.⁵ ............................................. A61F 9/02
[52] U.S. Cl. .................................................... 2/10
[58] Field of Search ............... 2/10, 421, 424, 426, 2/432; 24/598, 665

[56] References Cited

U.S. PATENT DOCUMENTS

| | | | |
|---|---|---|---|
| 2,266,967 | 12/1941 | Fuller | 2/10 |
| 2,631,286 | 3/1953 | Bowers | 2/8 |
| 3,577,564 | 5/1971 | Hill | 2/10 |
| 4,686,712 | 8/1987 | Spiva | 2/10 |

FOREIGN PATENT DOCUMENTS

| | | |
|---|---|---|
| 847458 | 6/1938 | France . |
| 7308921 | 10/1974 | France . |
| 56-74595 | 5/1981 | Japan . |

*Primary Examiner*—Werner H. Schroeder
*Assistant Examiner*—D. Price
*Attorney, Agent, or Firm*—Bachman & LaPointe

[57] ABSTRACT

This invention relates to a fastener for securing goggles tightly to a motor-cyclist's helmet.

The fastener comprises a support 4 fixed to each side of the helmet, beside the face aperture, a removable stud-piece 5 having an off-center mushroom-headed stud 15 and a buckle 6 attached to the free end of one of the two elastic straps 2 of the goggles.

The stud-piece 5 may be clipped into the support 4 either way round, to adjust the position of the stud 15. The buckle 6 prevents an aperture 21 which enables the buckle to be fixed onto the stud. One buckle 6 has a clip notch 22 which releasably maintains the buckle on the stud, while the other has only a circular aperture 21 to facilitate undoing the fastener.

10 Claims, 2 Drawing Sheets

ADJUSTABLE FASTENING FOR SECURING GOGGLES TO A HELMET

BACKGROUND OF THE INVENTION

This invention relates to a fastener for securing goggles and in particular a fastener for securing goggles to a motor-cyclist's helmet.

Not all motor-cyclist's helmet includes a visor of transparent plastics material for protecting the eyes of the wearer. In the absence of screen, it is therefore common to wear goggles of plastics material, which may be tinted or plain, and held in place laterally by straps of elastic material, themselves secured to the two sides of the helmet.

During competitions or cross-country races, the motor-cyclist must be able to put his goggles on, or remove them, very easily and very rapidly. In particular, he must be able to undo them with one hand only, while continuing to drive this motor-cycle and keeping the other hand on the accelerator handle.

DESCRIPTION OF THE PRIOR ART

Goggles of this kind are known, having straps of elastic material of which at least one end is secured to the helmet by strips of self-adhesive material known under the commercial name of "Velcro" but this system is unsatisfactory. In practice, competitions and especially cross-country races take place in difficult conditions, in mud and dust, and in these conditions the self-adhesive strips are rapidly filled with dust and gravel and can no longer be used adequately. Moreover, the self-adhesive strips are not designed to withstand strong traction. Now, the goggles must be held pressed against the motor-cyclist's face to avoid any risk of dust penetrating beneath them and so the straps must be stretched very tightly on each side of the helmet.

OBJECTS OF THE INVENTION

A first object of the invention is to provide a fastener for securing goggles to a motor-cyclist's helmet, which enables the goggles to be put on and taken off very rapidly.

A second object of the invention is to provide a fastener which enables the goggle straps to be stretched very tightly and to adjust the tension.

A general object of the invention is to provide the combination of a helmet and goggles including such a fastener.

SUMMARY OF THE INVENTION

The present invention provides a fastener for detachably securing a strap of a pair of goggles to the side of a motor-cyclist's helmet, said fastener comprising
 a support for fixing to the helmet,
 a fastener stud-piece for fixing detachably and reversibly to said support in first and second alternative positions,
 and a buckle for attaching to an end of said strap and for cooperating with said stud-piece, whereby to secure said strap detachably to the helmet.

DESCRIPTION OF THE DRAWINGS

Other features and advantages of the invention will appear from the following description of an embodiment thereof given by way of example, with reference to the accompanying drawings, in which.

DESCRIPTION OF THE PREFERRED EMBODIMENTS

Figure 1:
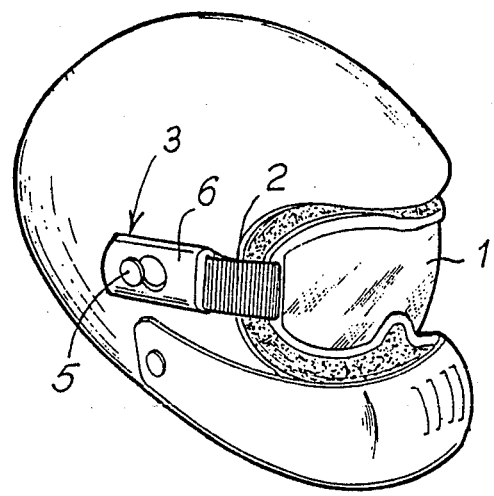
FIG. 1 is a perspective view of a pair of goggles fixed by a fastener onto a motorcycling helmet in accordance with the present embodiment of the invention.

FIG. 1 shows a combination comprising a helmet and screen 1 secured together by fasterners, in accordance with this embodiment of the invention. In the embodiment illustrated, the helmet is a motor-cyclist's helmet and the screen 1 comprises a pair of motor-cyclist's goggles. The goggles are of the kind having at least one protective lens, which may be tinted or plain, mounted in a frame of plastics material, and provided at each side with respective elastic strap 2. The two free ends of the elastic straps are secured to respective fastener elements 3. Each of the fastener elements 3 comprises a fixed support 4, a removable fastener stud-piece 5 and a buckle 6 for cooperating with the stud-piece 5 to do up or undo the fastener.

Figure 2:
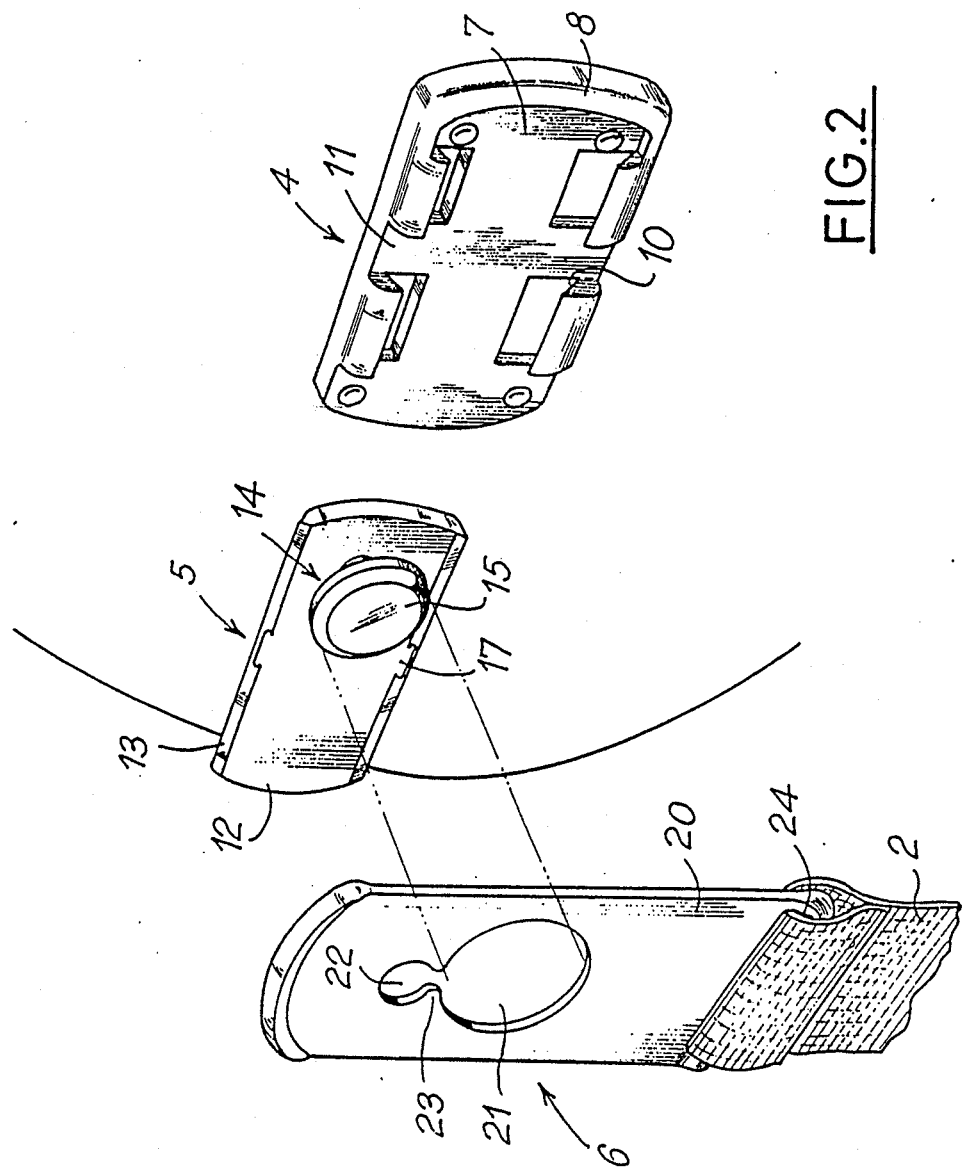
FIG. 2 is an exploded detail view of the fastener of FIG. 1.

As shown in FIG. 2, the fixed support 4 is mounted on the helmet and comprises a generally rectangular plate 7 whose two ends are convex. The two longitudinal sides of the plates are provided with upstanding projections with integral inwardly extending lips, the inner faces of the projections being inclined, whereby to define a slider grip 10. One end of the plate 7 is also provided with an upstanding rim 8 which extends round to the sides of the plate, the rim 8 forming an abutment. The slider grips 10 on each longitudinal side of the fixed support are interrupted over a short internal, so as to present a clip notch 11 disposed substantially in the mid-length of the fixed support 4.

The fastener stud-piece 5 comprises a thin substantially rectangular plate 12, whose two ends are convex. The two longitudinal sides of the plate are bevelled and the dimensions of the plate are such that it can slide on the plate 7 between the slider grips 10 until it abuts against the base of the fixed support 7. The plate 12 is solid with a stud 14, disposed substantially on the longitudinal meadian line of the plate, its axis being slightly off-centre. The stud 14 comprises a mushroom head 15 and a stalk 16. The stalk 16 is in the shape of a short cylinder, and the head 15 is a disc whose diameter is larger than that of the stalk 16. The height of the stalk 16 is chosen for cooperation with the buckle 6.

The stalk 16 of the stud is provided with two parallelopiped cavities 18 which are diametrically opposite each other and open towards each length of the plate 12.

Moreover the two bevelled sides 13 of the plate 12 are provided at their mid-points with a projection 17 designed to cooperate with the clip notch 11 when the stud-piece 5 is slipped into the fixed support 4.

Figures 3, 4:
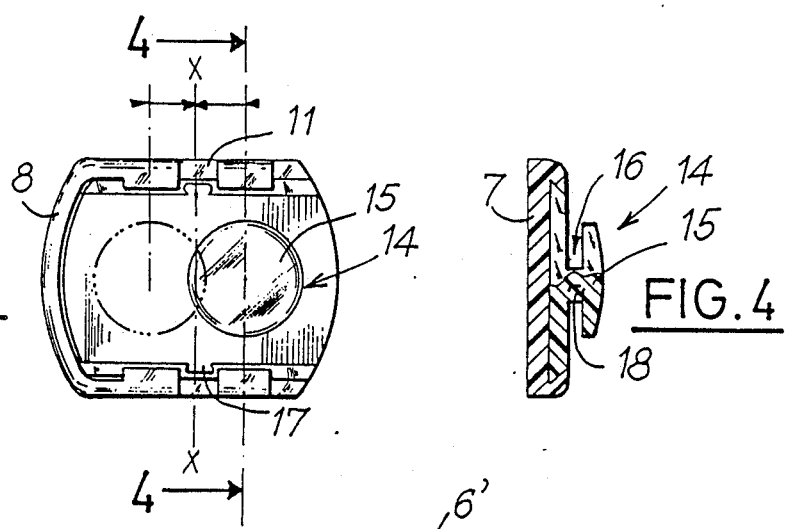
FIG. 3 is a plan view of an element of the fastener which is disposed on the helmet.
FIG. 4 is a sectional view of the fastener element of FIG.3 along the line 4—4.

The removable stud-piece 5 can slide in the fixed support 4 and it may be turned round and inserted by either end as desired. Consequently, as the stud 14 is disposed off-centre on the stud-piece 5, a two-position adjustment is possible between a first position (shown in broken lines in FIG. 3) in which the stud 14 is closer to the closed end of the fixed support 4, that is to say the end having the abutment 8, and a second position in which the stud 14 is further away from this closed end.

As shown in FIG. 2, the buckle 6 comprises a thin plate 20 of generally rectangular shape but whose two ends are convex. The length and width of this buckle are greater than the total length and width of the fixed support 4. The buckle presents a free end and an end connected to the part to be fixed, in the case of goggles, to the elastic strap 2. To this end, the plate 20 is provided with a slot 24 through which the strap 2 passes. The plate 20 presents a circular aperture 21 whose diameter is very slightly greater than that of the stud head 15, so that the stud head may be passed through the aperture 21. As mentioned above, the thickness of the buckle is such that when it mates with the stud-piece 5, it can be placed against the stalk 16 underneath the lower face of the stud head 15.

In addition, the aperture 21 is provided with a clip notch 22 disposed towards the free end of the plate 20. This clip notch 22 extends through the plate 20 in a C-shape opening into the aperture 21. It defines two clip lugs 23 at the intersection with the aperture 21.

Figure 5:
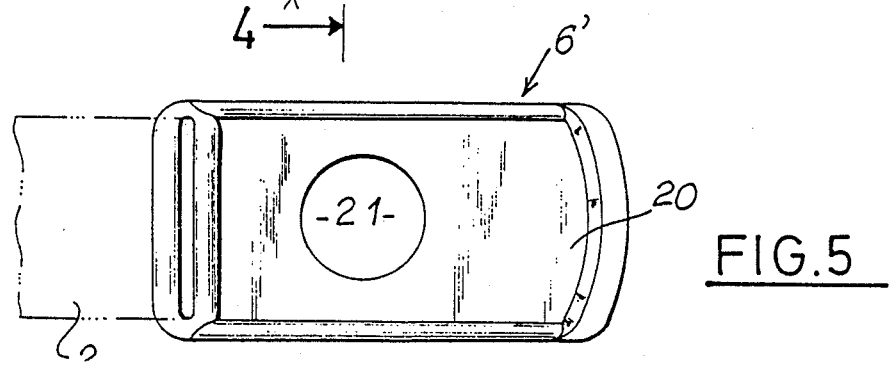
FIG. 5 is plan view of an alternative buckle element of the fastener which is secured on a strap of the goggles.

An alternative type of buckle 6' is illustrated in FIG. 5; it is identical to the buckle 6 of FIG. 2 except that it does not have a clip notch 22.

One of the fixed supports 4 is disposed on each side of the helmet, adjacent to the face aperture substantially at the level of the wearer's eyes. The fixed supports 4 are so placed that their closed ends are disposed towards the face aperture of the helmet. The stud-pieces 5 are then slipped into place on the supports and clipped in by the clip projections 17 into the clip notches 11. The goggles have right and left side straps (relative to the head of the motor-cyclist) whose ends are provided respectively with buckles 6 and 6'. The goggles are fixed by their respective buckles 6, 6' onto the stud-pieces 5, and the clip lugs 23 of the buckle 6 are brought to fit into the clip cavities 18 of the stud 14 under the tension of the strap 2. On the other side the inner edge of the aperture 21 of the buckle 6' is brought to rest against the stalk 16 of the stud, once more under the tension of the strap 2. When the motor-cyclist wishes to remove his goggles, he can do so with one hand, the left hand grasping the buckle 6' and pulling it off the stud-piece 5, whereas the goggles remain attached by the buckle 6 and hang vertically on the side of the helmet (as shown in FIG. 2). The goggles remain attached more readily due to the clip notch 22.

Preferably, the fixed support 4 and stud-piece 5 are made of rigid, plastics material, such as polypropylene, and the buckles 6, 6' are made of flexible plastics material, such as polyurethane.

We claim:

1. A fastener for detachably securing a strap of a pair of goggles to the side of a motor-cyclist's helmet, said fastener comprising a support for fixing to the helmet,
a fastener stud-piece for fixing detachably and reversibly to said support in first and second alternative positions,
and a buckle for attaching to an end of said strap and for cooperating with said stud-piece, whereby to secure said strap detachably to the helmet.

2. A fastener as claimed in claim 1, wherein said support comprises a generally rectangular plate whose two longitudinal sides and one of whose ends present projections forming slider grips and an abutment respectively, each lateral grip presenting a clip notch.

3. A fastener as claimed in claim 2, wherein said stud-piece comprises a generally rectangular plate which is solid with a stud disposed substantially on the longitudinal median line of the plate and whose axis is off-centre relative to the plate so that the stud-piece may be fixed to the support detachably and reversibly in a selected one of alternative first and second positions, said stud being closer to said abutment in said first position, and being more remote from said abutment in said second position.

4. A fastener as claimed in claim 3, wherein said stud comprises a shank on which is disposed an enlarged mushroom head.

5. A fastener as claimed in claim 4, wherein said buckle comprises a generally parallelopiped plate defining an aperture which is slightly larger than said head of the stud, whereby said head may pass through said aperture.

6. A fastener as claimed in claim 5, wherein said plate defines a clip notch extending from said aperture towards a free end of said plate for receiving and detachably retaining said shank of the stud.

7. A fastener as claimed in claim 1, wherein said buckle is made of a flexible plastics material and said support and said stud-piece are made of rigid plastics material.

8. A combination of a helmet and a pair of goggles including at least one fastener for detachably securing goggles to said helmet wherein said helmet defines a face aperture, a support being fixed to the side of said helmet adjacent said face aperture, a strap of said goggles being elastic and presenting a free end, and a buckle being attached to said free end of said strap.

9. A combination as claimed in claim 8, wherein said goggles present two of said elastic straps, and including two of said fasteners, the supports of said fasteners being fixed to respective sides of said helmet adjacent said face aperture and the buckles of said fastener being attached to the free ends of respective ones of said straps.

10. A combination as claimed in claim 9, wherein the buckle of one of said fasteners defines an aperture having a clip notch for receiving and detachably a shank of a fastener stud-piece, and the buckle of the other fastener defines, a circular aperture for cooperating with said stud piece.

* * * * *